(12) United States Patent
Mou et al.

(10) Patent No.: US 10,962,452 B2
(45) Date of Patent: Mar. 30, 2021

(54) ACTUATING AND SENSING MODULE (71) Applicant: Microjet Technology Co., Ltd., Hsinchu (TW)

(72) Inventors: Hao-Jan Mou, Hsinchu (TW); Shih-Chang Chen, Hsinchu (TW); Chi-Feng Huang, Hsinchu (TW); Yung-Lung Han, Hsinchu (TW); Chun-Yi Kuo, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 203 days.

(21) Appl. No.: 16/276,225

(22) Filed: Feb. 14, 2019

(65) Prior Publication Data
US 2019/0331558 A1  Oct. 31, 2019

(30) Foreign Application Priority Data
Apr. 27, 2018 (TW) ................................. 107114581

(51) Int. Cl.
*G01N 1/22* (2006.01)
*G01N 33/00* (2006.01)

(52) U.S. Cl.
CPC ......... *G01N 1/2273* (2013.01); *G01N 33/004* (2013.01); *G01N 33/0047* (2013.01); *G01N 2001/2276* (2013.01)

(58) Field of Classification Search
CPC ......... G01N 1/2273; G01N 2001/2276; G01N 33/004; G01N 33/0047
See application file for complete search history.

(56) References Cited

U.S. PATENT DOCUMENTS

| 8,721,303 | B2* | 5/2014 | Fujisaki | F04B 43/046 |
| | | | | 417/413.2 |
| 10,168,239 | B2* | 1/2019 | Al-Hemyari | G01N 33/0016 |
| 10,663,387 | B2* | 5/2020 | Mou | F04B 39/123 |

(Continued)

FOREIGN PATENT DOCUMENTS

| CN | 101561413 A | 10/2009 |
| EP | 2905673 A2 | 8/2015 |

(Continued)

OTHER PUBLICATIONS

Extended European Search Report for European Application No. 19157118.1, dated Aug. 28, 2019.

*Primary Examiner* — Natalie Huls
(74) *Attorney, Agent, or Firm* — Birch, Stewart, Kolasch & Birch, LLP (57) ABSTRACT

An actuating and sensing module includes a first substrate, a second substrate, an actuating device and a sensor. The first and second substrates are stacked on each other as a gas flow channel is formed therebetween. The gas inlet, the gas flow channel and the gas outlet are in communication with each other to define a gas flow path. The actuating device is disposed in the gas outlet of the second substrate and electrically connected to a control circuit to obtain driving power. The sensor is disposed in the gas flow path and misaligned with the gas inlet. The sensor is spaced apart from the actuating device and is electrically connected to the control circuit. Being driven by the actuating device, the gas is transported from the outside into the gas flow path and monitored by the sensor.

18 Claims, 8 Drawing Sheets

(56) References Cited

U.S. PATENT DOCUMENTS

| | | | |
|---|---|---|---|
| 10,677,773 B2 * | 6/2020 | Mou | G01N 33/004 |
| 10,775,276 B2 * | 9/2020 | Mou | G01N 1/14 |
| 2007/0044577 A1 * | 3/2007 | Trakumas | G01N 1/2208 |
| | | | 73/863.22 |
| 2010/0031730 A1 * | 2/2010 | Van Uitert | A61B 5/082 |
| | | | 73/23.3 |
| 2010/0139389 A1 * | 6/2010 | Morita | G01F 5/00 |
| | | | 73/204.11 |
| 2014/0294046 A1 * | 10/2014 | Le Neel | G01W 1/02 |
| | | | 374/143 |
| 2014/0377099 A1 * | 12/2014 | Hsueh | F04B 49/22 |
| | | | 417/413.2 |
| 2015/0219608 A1 * | 8/2015 | Choi | G06F 1/1694 |
| | | | 73/23.2 |
| 2016/0076530 A1 * | 3/2016 | Chen | F04B 43/046 |
| | | | 417/413.2 |
| 2016/0103082 A1 * | 4/2016 | Kimura | G01N 33/005 |
| | | | 73/25.01 |
| 2016/0327532 A1 * | 11/2016 | Bather | G01N 33/0009 |
| 2018/0120278 A1 * | 5/2018 | Hoorfar | G01N 33/497 |
| 2019/0011416 A1 * | 1/2019 | Worth | G01N 33/0006 |
| 2019/0094146 A1 * | 3/2019 | Tao | G01N 33/0037 |
| 2019/0154551 A1 * | 5/2019 | Richter | G01N 1/2273 |
| 2019/0302075 A1 * | 10/2019 | Mou | F04B 43/046 |
| 2019/0353157 A1 * | 11/2019 | Mou | F04B 45/047 |

FOREIGN PATENT DOCUMENTS

| | | |
|---|---|---|
| TW | M553479 U | 12/2017 |
| TW | M554563 U | 1/2018 |

* cited by examiner

ACTUATING AND SENSING MODULE

FIELD OF THE INVENTION

The present disclosure relates to an actuating and sensing module, and more particularly to an actuating and sensing module sensing gas by means of gas circulation.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these substances in the environment can cause human health problems or can even harm the life. Therefore, it has become an important issue for every country to develop and implement environmental air quality monitoring technology.

However, the conventional gas detection equipment for example an air cleaning and filtering apparatus is bulky in volume and is not suitable to be carried by the user. Consequently, it is difficult for the user to obtain the real-time air quality information relating to the surrounding environment, and the user is still likely to be exposed to an environment with harmful gases. Therefore, an urgent problem that needs to be solved is how to obtain the gas quality information relating to the surrounding environment at anytime and anywhere.

However, since the conventional gas detection equipment fails to provide the waterproof and dustproof functions, some problems occur. If moisture or liquid is introduced into the equipment during the process of transferring the gas, the outputted gas tends to contain the moisture, so that the electronic components utilized to sense the gas is possibly damped, rusted or damaged. Moreover, the conventional gas detection equipment fails to provide dustproof function. If dust is introduced into the gas detection equipment during the process of transferring the gas, the components are possibly damaged and the gas transportation efficiency is reduced. Therefore, another urgent problem that needs to be solved is how to make the gas detection equipment has the waterproof and dustproof benefits.

Therefore, there is a need of providing an actuating and sensing module for allowing a gas detection apparatus or equipment to achieve small-size, miniature, silent, waterproof and dustproof benefits in order to eliminate the above drawbacks.

SUMMARY OF THE INVENTION

An object of the present disclosure provides an actuating and sensing module. While the gas fluctuation is generated by the high frequency operation of the piezoelectric membrane, a pressure gradient is generated in the designed flow channel and the gas flows at a high speed. Moreover, since there is an impedance difference between the feeding direction and the exiting direction, the gas can be transported from the inlet side to the outlet side. It benefits to solve the problems that the apparatus or equipment utilizing the conventional gas transportation device has a large volume, is difficult to be thinned, fails to achieve the purpose of portability, and has loud noises.

Another object of the present disclosure provides an actuating and sensing module with waterproof and dustproof functions. By being equipped with a protective film to filter the moisture and the dust, it benefits to solve the problems that while the moisture or the dust is introduced into the conventional gas transportation device during the process of transferring the gas, the components are possibly damaged and the gas transportation efficiency is reduced.

In accordance with an aspect of the present disclosure, an actuating and sensing module is provided. The actuating and sensing module includes a first substrate, a second substrate, at least one actuating device and at least one sensor. The first substrate includes at least one control circuit. The second substrate includes a gas inlet and a gas outlet. The first substrate and the second substrate are stacked on each other as a gas flow channel is formed therebetween. The gas inlet, the gas flow channel and the gas outlet are in communication with each other to define a gas flow path. The actuating device is disposed in the gas outlet of the second substrate and electrically connected to the control circuit. The sensor is disposed in the gas flow path and misaligned with the gas inlet. The sensor is spaced apart from the actuating device and is electrically connected to the control circuit. The actuating device is enabled to drive outside gas to flow from the exterior of the actuating and sensing module into the gas flow channel through the gas inlet, and the gas flows through the sensor and is discharged out through the gas outlet, so that the gas is circulated in the gas flow path and monitored by the sensor in the meantime.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
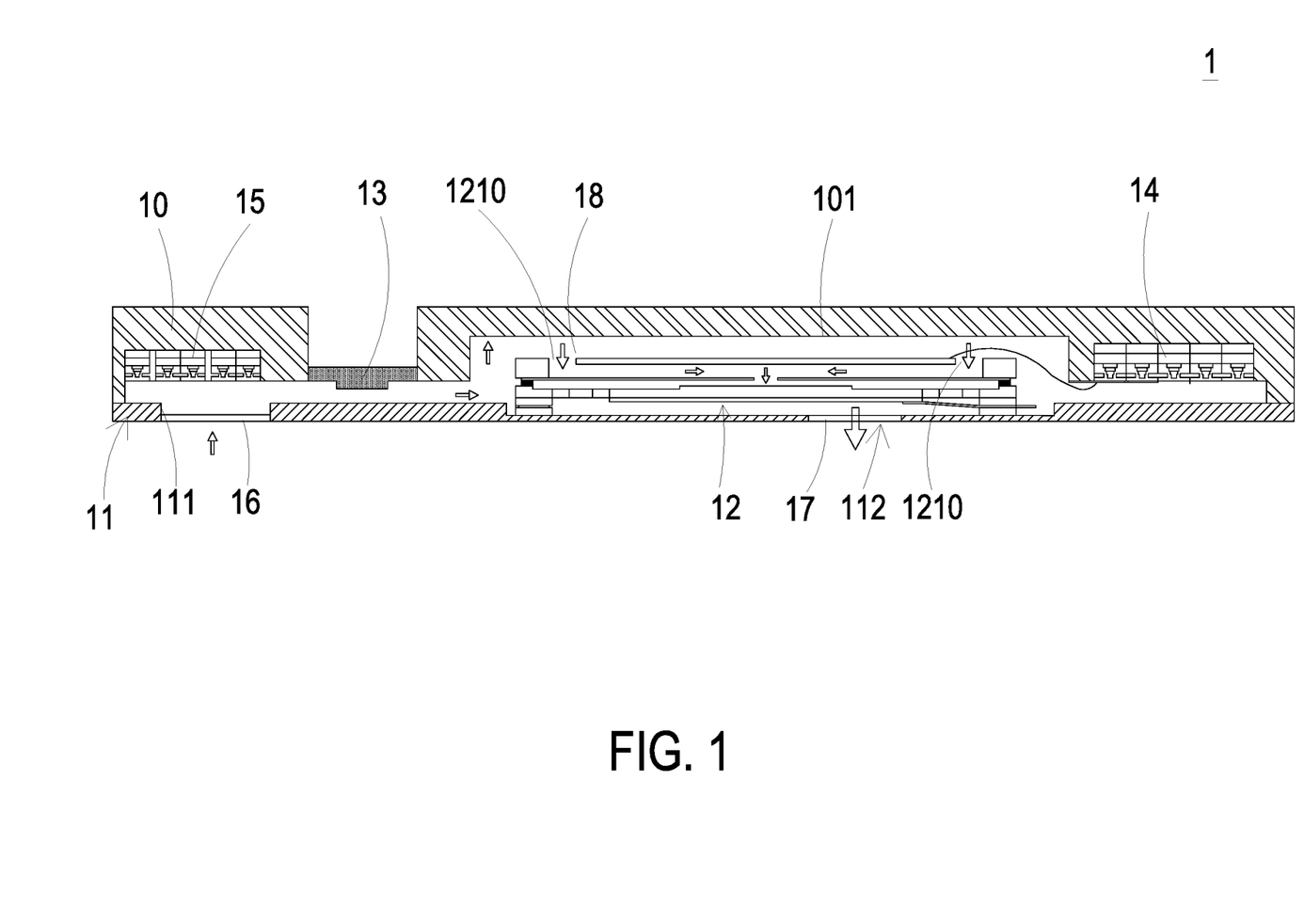
FIG. 1 is a cross-sectional view illustrating an actuating and sensing module according to one embodiment of the present disclosure.

Please refer to FIG. 1. The present discourse provides an actuating and sensing module 1 including at least one first substrate 10, at least one second substrate 11, at least one actuating device 12, at least one sensor 13, at least one gas inlet 111, at least one gas outlet 112, at least one gas flow channel 18, at least one gas flow path and at least one gas.

The number of the first substrate 10, the second substrate 11, the gas inlet 111, the gas outlet 112, the gas flow channel 18, the gas flow path and the gas is exemplified by one for each in the following embodiments but not limited thereto. It is noted that each of the first substrate 10, the second substrate 11, the gas inlet 111, the gas outlet 112, the gas flow channel 18, the gas flow path and the gas can also be provided in plural numbers.

The present disclosure provides an actuating and sensing module, which is used to sense the air quality relating to the surrounding environment and has the waterproof, dustproof and silent benefits. The actuating and sensing module may be used in a mobile phone, a tablet, a wearable device or any similar portable electronic device constructed to contain CPU, RAM and other components. Please refer to FIG. 1, which is a cross-sectional view illustrating an actuating and sensing module according to a first embodiment of the present disclosure. As shown in the drawing, the actuating and sensing module 1 includes a first substrate 10, a second substrate 11, an actuating device 12 and a sensor 13. The first substrate 10 has at least one control circuit disposed therein. In the embodiment, the first substrate 10 has a first control circuit 14 and a second control circuit 15, both of which are integrated circuits. The first control circuit 14 is electrically connected to the actuating device 12, so as to drive the actuating device 12 and provide driving power. The second control circuit 15 is electrically connected to the sensor 13, so as to calculate and process the sensed data generated by the sensor 13 and provide driving power. In other embodiments, the first substrate 10 includes one control circuit merely, and the single control circuit is electrically connected to the actuating device 12 and the sensor 13 so as to actuate them, provide driving power, and calculate and process the sensed data generated by the sensor 13.

The second substrate 11 includes a gas inlet 111 and a gas outlet 112 running therethrough. The actuating device 12 is disposed on the gas outlet 112. While the first substrate 11 and the second substrate 12 are stacked together, a gas flow channel 18 is formed between the first substrate 11 and the second substrate 12. Moreover, the gas inlet 111, the gas flow channel 18 and the gas outlet 112 are in communication with each other sequentially, so as to form a gas flow path. In the embodiment, the first substrate 11 further includes a recess 101. The gas flow channel 18 is formed between the recess 101 of the first substrate 10 and the second substrate 11, so as to achieve a structural design that is more space-saving. Meanwhile, the thickness of the overall structure of the actuating and sensing module 1 can be reduced, so as to achieve a thin and light volume.

In this embodiment, the first substrate 10 is a chip and can be for example but not limited to an application-specific integrated circuit (ASIC) chip or a system-on-chip (SOC) chip. The second substrate 11 is a chip cover plate and packaged on the first substrate 10. The recess 101 is formed on the first substrate 10 by a semiconductor process. The first control circuit 14 and the second control circuit 15 are packaged on the first substrate 10 by a semiconductor process. The gas inlet 111 and the gas outlet 112 are formed on the second substrate 11 by a semiconductor process. Moreover, the actuating device 12 is packaged on the gas outlet 112 of the second substrate 11 by a semiconductor process.

Please refer to FIG. 1 again. In the embodiment, the actuating device 12 is disposed to cover the gas outlet 112 of the second substrate 11, and electrically connected to the first control circuit 14, so as to obtain driving power. The actuating device 12 is used for driving the gas to flow. The actuating device 12 includes a plurality of inlets 1210. As being driven, the gas within the gas flow channel 18 flows into the actuating device 12 though the inlets 1210, then being discharged out the actuating and sensing module 1 through the gas outlet 112. Consequently, a negative pressure is generated in the gas flow channel 18 so as to inhale outside gas into the actuating and sensing module 1 through the gas inlet 111. Above-mentioned actions are repeatedly done to achieve continuous gas transportation. In the embodiment, the actuating device 12 is a resonant-type piezoelectrically-actuated gas pump. The detailed structure of the actuating device 12 will be further described as follows.

Please refer to FIG. 1 again. The sensor 13 may be adjacent to the gas inlet 111 and is disposed within the gas flow path, which is formed by sequentially communicating the gas inlet 111, the gas flow channel 18 and the gas outlet 112 with each other, so that the sensor 13 can be used for sensing a concentration of at least one detecting target contained in the gas introduced to the gas flow path at the first moment. In the embodiment, the sensor 13 is disposed on the first substrate 10 and adjacent to the gas inlet 111 of the second substrate 11. Moreover, the sensor 13 is misaligned with the gas inlet 111, so that the gas introduced into the gas inlet 111 does not directly flow towards a sensing surface of the sensor 13. In this circumstance, a stable gas flow passing through the sensing surface of the sensor 13 could be maintained, and the detection accuracy of the sensor 13 would not be affected. In addition, the sensor 13 is spaced apart from the actuating device 12, so that detection of the sensor 13 would not be affected by the heat generated thereby. In the embodiment, the sensor 13 is formed on the first substrate 10 by the semiconductor process and electrically connected to the second control circuit 15, so as to transmit the sensed data to the second control circuit 15. Consequently, the sensed data can be calculated and processed by the second control circuit 15. The sensor 13 can include at least one sensor selected from the group consisting of an oxygen sensor, a carbon monoxide sensor, a carbon dioxide sensor, a temperature sensor, an ozone sensor, a volatile organic compound sensor and a combination thereof, but not limited thereto. It can be varied according to the practical requirements.

In the embodiment, a pressure differences is generated by actuation of the actuating device 12. Consequently, the gas is inhaled into the gas flow channel 18 through the gas inlet 111 of the second substrate 11 from the outside of the actuating and sensing module 1, and transferred to the sensor 13. After flowing through the sensor 13, the gas is discharged out of the actuating and sensing module 1 through the gas outlet 112 of the second substrate 11. Thus, the sensor 13 can be utilized to monitor the concentration of at least one detecting target contained in the ambient air, so as to obtain the real-time information relating to the monitoring of ambient air. At the same time, the speed of the gas circulation is accelerated by the actuating device 12, and the sensor 13 can obtain the most immediate information relating to the ambient air. That is, once it is detected that the surrounding environment contains toxic gases or dangerous gases, the user can be notified to take immediate protective measures to avoid the gas poisoning and the gas explosion.

Please refer to FIG. 1 again. The actuating and sensing module 1 further includes at least one first protective film 16 and at least second protective film 17. The first protective film 16 is disposed to cover the gas inlet 111. The second protective film 17 is disposed to cover the gas outlet 112. Since the first protective film 16 and the second protective film 17 have a waterproof, dustproof and gas-allowed film structure, the arrangement prevents the moisture and dust from entering the gas flow channel 18 from the gas inlet 111, and also prevents the moisture and dust from entering the gas flow channel 18 backward from the gas outlet 112. Thus, the inner space of the gas flow channel 18 can be maintained in a dry and dust-free situation. It benefits to prevent the components disposed inside the gas flow channel 18 from the damage and the rusty caused by the moisture or the accumulated dust.

In an embodiment, the first protective film 16 and the second protective film 17 comply with the Rating IP64 of International Protection Marking (IEC 60529), i.e., Dust protection level 6 (Complete protection, No ingress of dust) and Water protection level 4 (Protection against Splashing of water: Water splashing against the enclosure from any direction shall have no harmful effect). In another embodiment, the first protective film 16 and the second protective film 17 comply with the Rating IP68 of International Protection Marking (IEC 60529), i.e., Dust protection level 6 and Water protection level 8 (Continuous immersion in water produces no harmful effects). In other embodiments, the first protective film 16 and the second protective film 17 comply with the Rating IP65, IP66 or IP67 of International Protection Marking (IEC 60529), but not limited thereto.

Figure 2A:
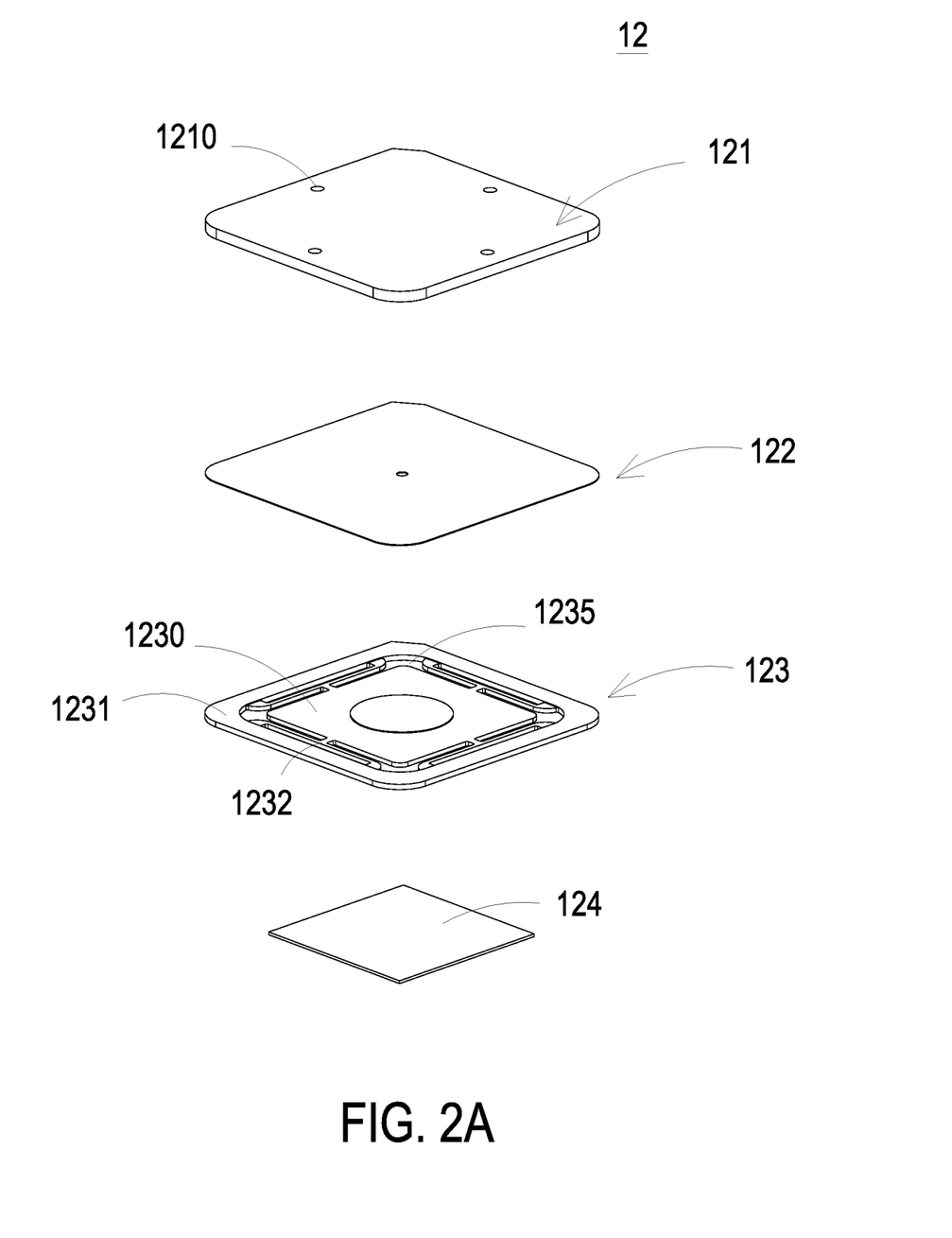
FIG. 2A is a schematic exploded view illustrating the actuating device of FIG. 1 and taken along a first viewpoint.
Figure 2B:
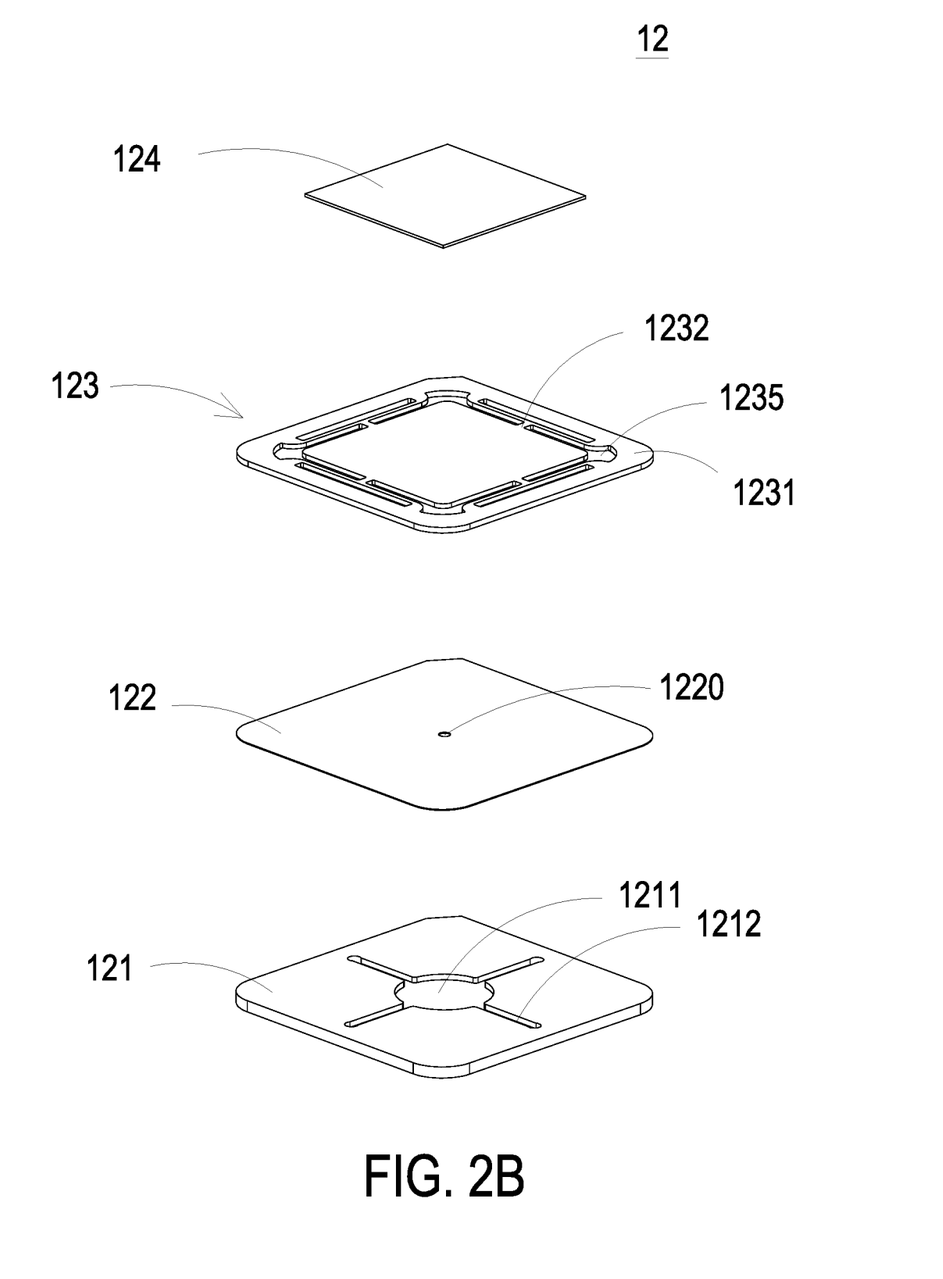
FIG. 2B is a schematic exploded view illustrating the actuating device of FIG. 1 and taken along a second viewpoint.

Please refer to FIGS. 2A and 2B. FIG. 2A is a schematic exploded view illustrating the actuating device of FIG. 1 and taken along a first viewpoint. FIG. 2B is a schematic exploded view illustrating the actuating device of FIG. 1 and taken along a second viewpoint. In the embodiment, the actuating device 12 is a resonant-type piezoelectrically-actuated gas pump. For describing and emphasizing the features of the structure, the structure of the actuating device 12 is decomposed, but not intended to illustrate that it is a detachable structure. As shown in the drawings, in the embodiment, the actuating device 12 includes an inlet plate 121, a resonance membrane 122, an actuating membrane 123 and a piezoelectric membrane 124. The inlet plate 121, the resonance membrane 122, the actuating membrane 123 and the piezoelectric membrane 124 are stacked on each other sequentially to be assembled as the actuating device 12. A compressing chamber 1221 (shown in FIG. 4A) is formed between the resonance membrane 122 and the actuating membrane 123. The type and structure of the actuating device 12 are not limited to those described above and can be varied according to the practical requirements.

Please refer to FIGS. 2A and 2B. In the embodiment, the plural inlets 1210 are formed on the inlet plate 121. In the embodiment, the number of the inlets 1210 is exemplified by four but not limited thereto. The number of the inlets 1210 can be arbitrarily varied according to the practical requirements. In response to the action of the atmospheric pressure, the gas can be inhaled into the actuating device 12 through the inlets 1210 from the outside of the actuating device 12. In the embodiment, the inlet plate 121 further includes a convergence chamber 1211 (shown in FIG. 2B) and the convergence chamber 1211 is in communication with the plural inlets 1210. In that, the gas is inhaled through the inlets 1210, transferred and converged to the convergence chamber 1211 for temporarily storing the gas and transferring the gas. The resonance membrane 122 includes a central aperture 1220 corresponding in position to the convergence chamber 1211, so as to transfer the gas to the compressing chamber 1221 (shown in FIG. 4A).

Figure 3A:
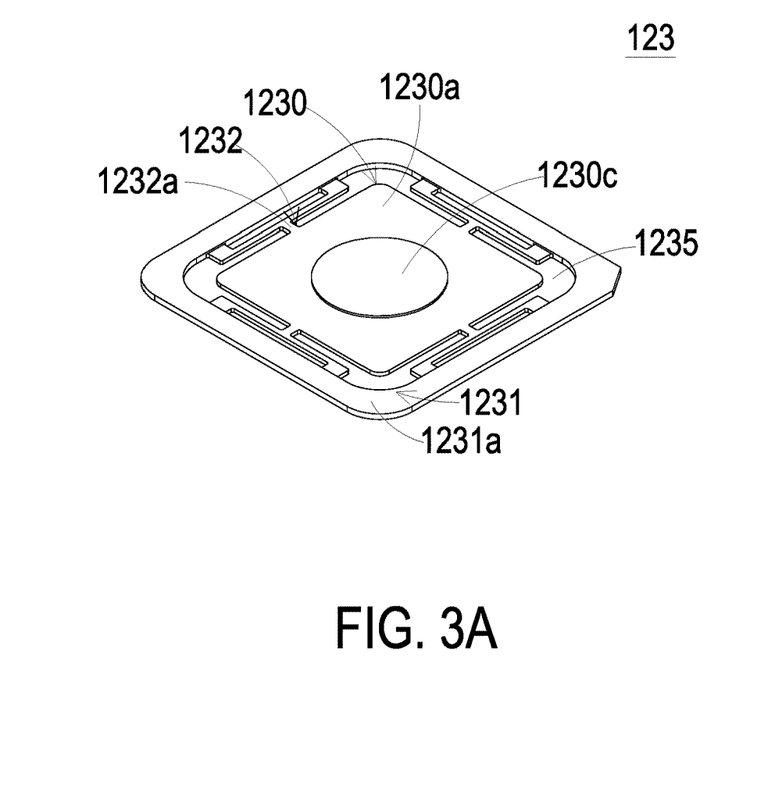
FIG. 3A is a schematic perspective view illustrating the actuating membrane of the actuating device of FIG. 2A and taken along the front side.
Figure 3B:
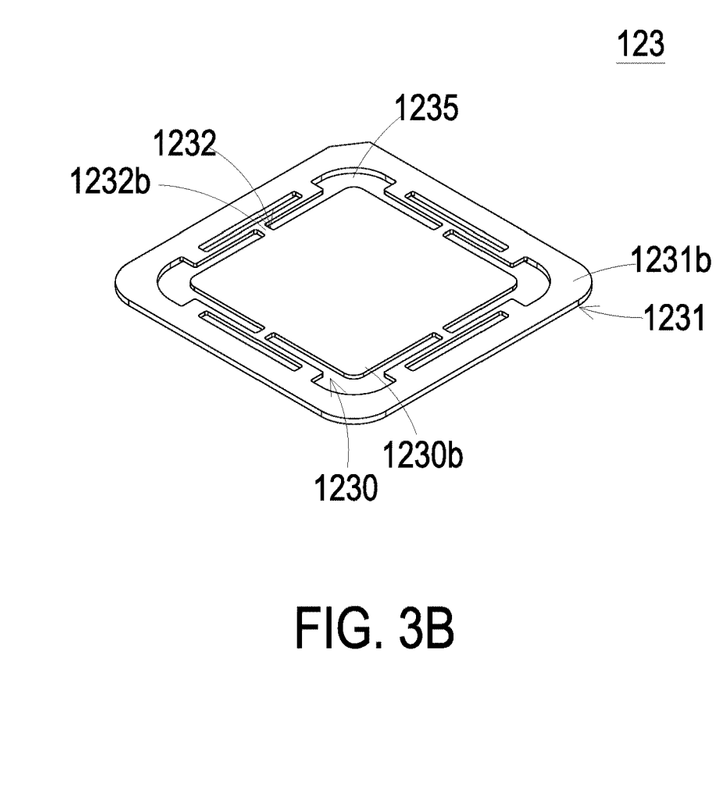
FIG. 3B is a schematic perspective view illustrating the actuating membrane of the actuating device of FIG. 2A and taken along the rear side.
Figure 3C:
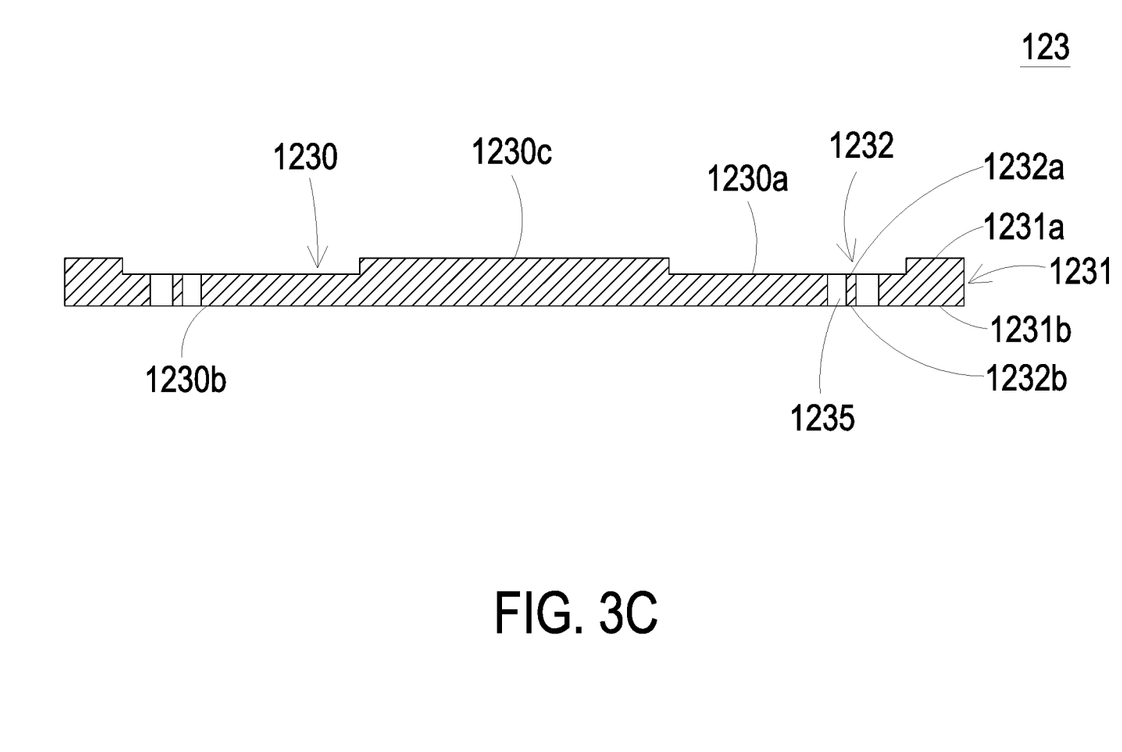
FIG. 3C is a schematic cross-sectional view illustrating the actuating membrane of the actuating device of FIG. 2A.

Please refer to FIGS. 2A to 3C. FIG. 3A is a schematic perspective view illustrating the actuating membrane of the actuating and sensing module of FIG. 2A and taken along the front side. FIG. 3B is a schematic perspective view illustrating the actuating membrane of the actuating and sensing module of FIG. 2A and taken along the rear side. FIG. 3C is a schematic cross-sectional view illustrating the actuating membrane of the actuating and sensing module of FIG. 2A. As shown in the drawings, in the embodiment, the actuating membrane 123 further includes a suspension part 1230, an outer frame 1231 and a plurality of the connection parts 1232. The plurality of the connection parts 1232 are connected between the suspension part 1230 and the outer frame 1231, while an end of each connection part 1232 is connected with the outer frame 1231 and another end of each connection part 1232 is connected with the suspension part 1230. Moreover, a vacant space 1235 is formed among each connection part 1232, the suspension part 1230 and the outer frame 1231 for allowing the gas to go through. The arrangement, the type and the number of the suspension part 1230, the outer frame 1231 and the connection parts 1232 are not restricted and can be varied according the practical requirements.

In the embodiment, the suspension part 1230 is a stepped structure. Namely, the suspension part 1230 includes a bulge 1230c disposed on the top surface 1230a of the suspension part 1230. The bulge 1230c can be but not limited to a circular convex structure. As shown in FIGS. 3A to 3C, a top surface of the bulge 1230c of the suspension part 1230 is coplanar with a top surface 1231a of the outer frame 1231, while the top surface 1230a of the suspension part 1230 is coplanar with a top surface 1232a of the connection part 1232. Moreover, there is a specified depth from top surface of the bulge 1230c of the suspension part 1230 and the top surface 1231a of the outer frame 1231 to the top surface 1230a of the suspension part 1230 and the top surface 1232a of the connection part 1232. As shown in FIGS. 3B and 3C, a bottom surface 1230b of the suspension part 1230, a bottom surface 1231b of the outer frame 1231 and a bottom surface 1232b of the connection part 1232 are coplanar with each other and form a flat plane, but not limited thereto.

Please refer to FIGS. 2A and 2B again. The piezoelectric membrane 124 is attached on the bottom surface 1230b of the suspension part 1230 of the actuating membrane 123, so that the actuating membrane 123 is enabled to vibrate along a vertical direction in a reciprocating manner and drive the resonance membrane 122 to vibrate. Thus, the pressure of the compressing chamber 1221 between the resonance membrane 122 and actuating membrane 123 is varied to transport the gas.

In the embodiment, when the piezoelectric membrane 124 is enabled to drive the actuating membrane 123, the gas is inhaled into the convergence chamber 1211 through the plural inlets 1210 of the inlet plate 121 and transferred to the compressing chamber 1221 through the central aperture 1220 of the resonance membrane 122 and flows out from the vacant space 1235 of the actuating membrane 123, so that the gas is introduced into the gas flow channel 18.

Figure 4A:
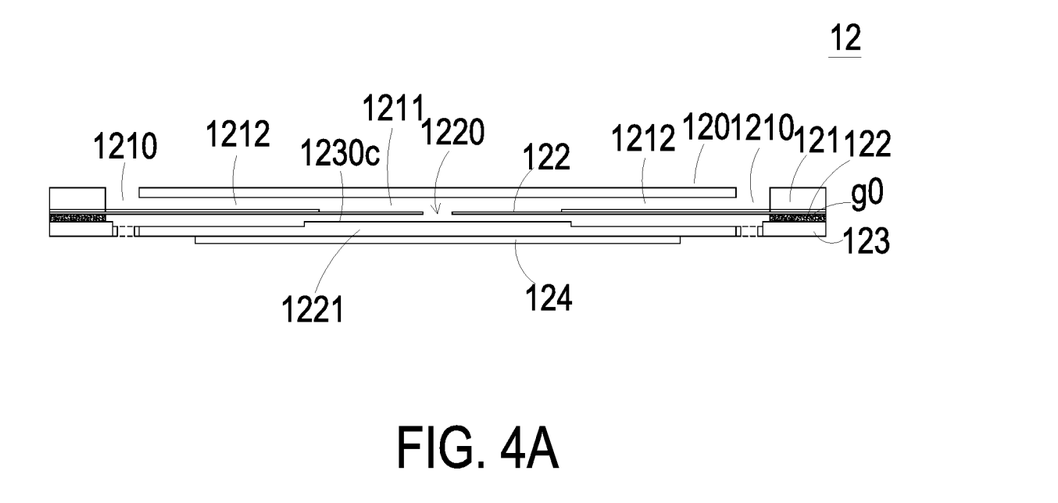
FIGS. 4A to 4E schematically illustrate the actions of the actuating device of FIG. 2B.
Figure 4B:
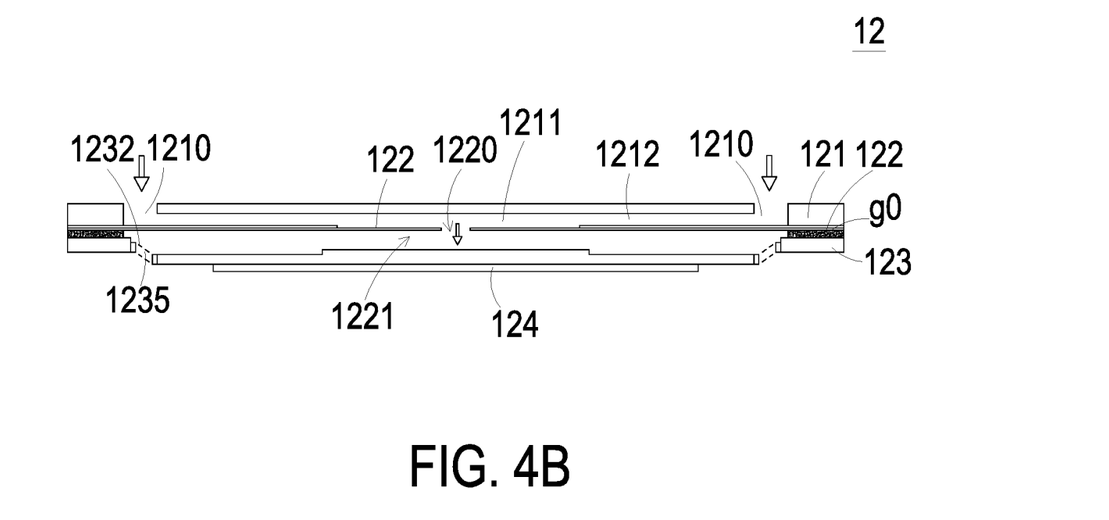

Please refer to FIGS. 2A, 2B and 4A to 4E. FIGS. 4A to 4E schematically illustrate the actions of the actuating and sensing module of FIG. 2B. Firstly, as shown in FIG. 4A, the actuating device 12 is formed by stacking the inlet plate 121, the resonance membrane 122, the actuating membrane 123 and the piezoelectric membrane 124 on each other sequentially. A spacer g0, which can be for example an adhesive layer, is disposed between the resonance membrane 122 and the actuating membrane 123 to keep a depth between the resonance membrane 122 and the bulge 1230c of the suspension part 1230 of the piezoelectric membrane 123. Thus, the gas can be transferred more quickly, the contact interference is reduced and the generated noise is largely reduced. In some other embodiments, the spacer g0 may be formed by thickening the outer frame 1231 of the actuating membrane 123 to make a gap formed between the resonance membrane 122 and the bulge 1230c of the suspension part 1230 while the actuating membrane 123 is assembled with the resonance membrane 122, but not limited thereto.

Please refer to FIGS. 4A to 4E. As shown in the drawings, a chamber for converging the gas is defined collaboratively by the central aperture 1220 of the resonance membrane 122 and the convergence chamber 1211 of the inlet plate 121. The compressing chamber 1221 is formed between the resonance membrane 122 and the actuating membrane 123 for temporarily storing the gas. Through the central aperture 1220 of the resonance membrane 122, the compressing chamber 1221 is in communication with the convergence chamber 1211. Through the vacant space 1235 between the connection parts 1232 of the actuating membrane 123, the peripheral regions of the compressing chamber 1221 are in fluid communication with the gas out 112 of the second substrate 11 (shown in FIG. 1).

Figure 4C:
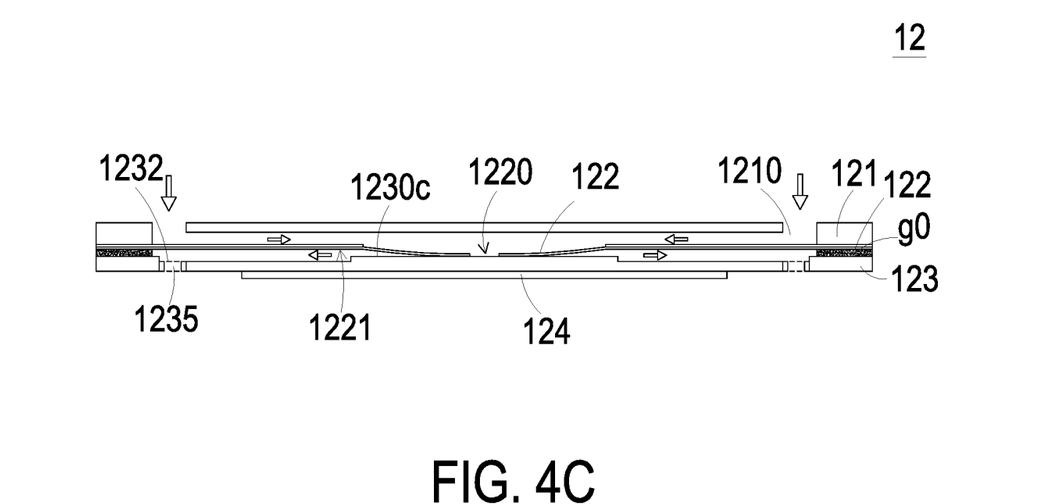
Figure 4D:
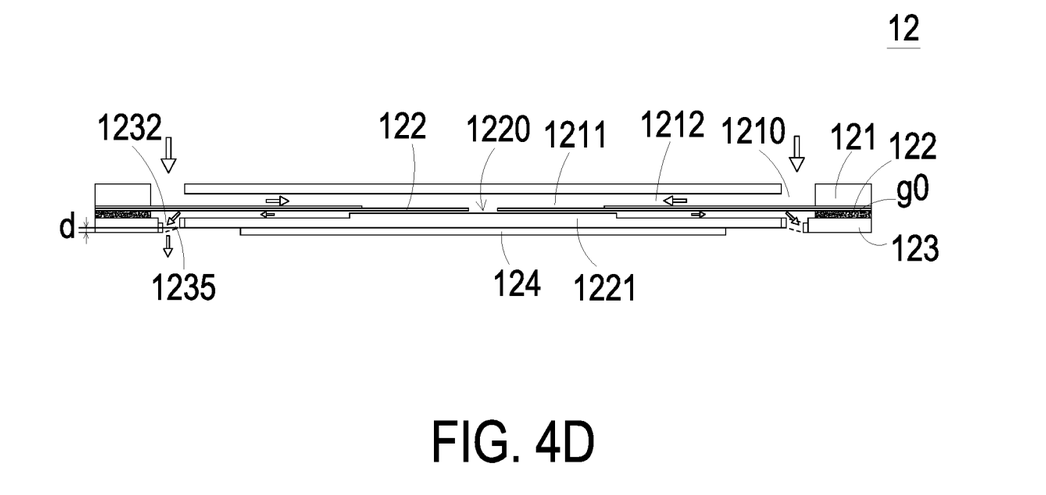
Figure 4E:
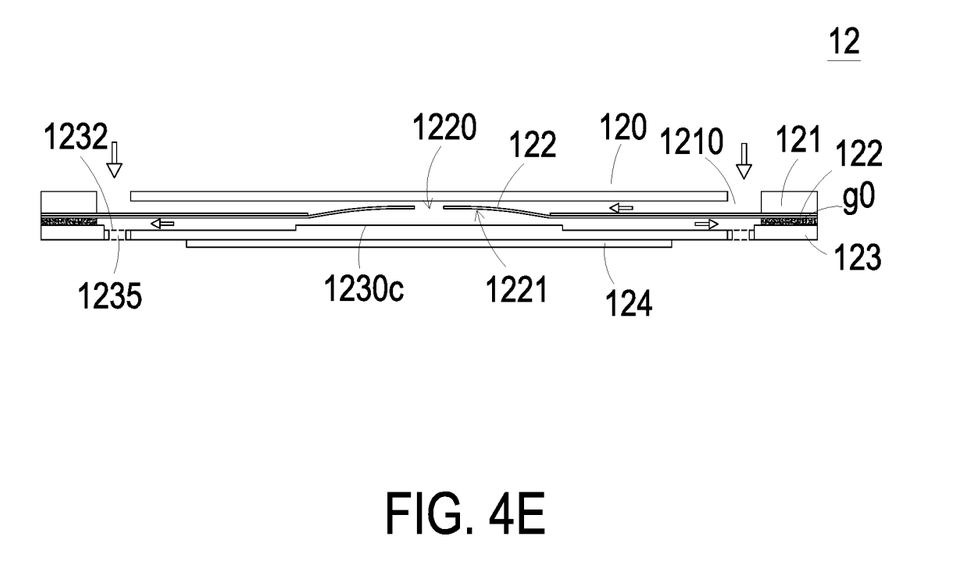

When the actuating device 12 is enabled, the actuating membrane 123 vibrates along a vertical direction in a reciprocating manner by using the connection part 1232 as a fulcrum. Please refer to FIG. 4B, when the actuating membrane 123 vibrates along a first direction in response to the applied voltage, the gas is inhaled through the plural inlets 1210 of the inlet plate 121 and converged into the convergence chamber 1211. Meanwhile, the gas is further transferred along the first direction into the compressing chamber 1221 through the central aperture 1220 of the resonance membrane 122. Afterward, as the actuating membrane 123 is enabled to drive the resonance membrane 122, the resonance of the resonance membrane 122 occurs. Consequently, the resonance membrane 122 vibrates along the vertical direction in the reciprocating manner. As shown in FIG. 4C, the resonance membrane 122 moves along the first direction to contact and attach on the bulge 1230c of the suspension part 1230 of the actuating membrane 123. Owing to the deformation of the resonance membrane 122 described above, a middle communication space of the compressing chamber 1221 is closed, and the volume of the compressing chamber 1221 is shrunk. Under this circumstance, the gas in the compressing chamber 1221 is pushed to move toward to peripheral regions of the compressing chamber 1221 and flowing along the first direction through the vacant space 1235 between the connection parts 1232 of the actuating membrane 123. As shown in FIG. 4D, the resonance membrane 122 has returned to its original position. The actuating membrane 123 vibrates along a second direction in response to the applied voltage. Consequently, the volume of the compressing chamber 1221 is continuously shrunk and the actuating membrane 123 vibrates along the second direction with a second direction displacement d, which makes the gas in the compressing chamber 1221 continuously pushed toward peripheral regions. Meanwhile, the gas is continuously transferred to be filtered through the first protective film 16 and the second protective film 17 (shown in FIG. 1) and inhaled into the convergence chamber 1211 from the inlets 1210 of the inlet plate 121. As shown in FIG. 4E, the resonance membrane 122 moves along the second direction, which is cause by the resonance of the second direction motion of the actuating membrane 123. Consequently, the gas is transferred from the convergence chamber 1211 into the compressing chamber 1221 through the central aperture 1220, transferred through the vacant space 1235 among the connection parts 1232 of the actuating membrane 123, and further transferred along the first direction to flow out of the actuating device 12. In this way, a pressure gradient is generated in the gas flow path of the actuating device 12 to facilitate the gas to flow at a high speed. Moreover, since there is an impedance difference between the feeding direction and the exiting direction, the gas can be transported from the inlet side to the outlet side. Even if a gas pressure higher than the atmosphere exists at the outlet side, the actuating device 12 still has the capability of pushing the gas to the outlet side while achieving the silent efficacy. In some embodiments, the vibration frequency of the resonance membrane 122 along the vertical direction in the reciprocating manner is identical to the vibration frequency of the actuating membrane 123. That is, the resonance membrane 122 and the actuating membrane 123 are synchronously vibrated along a same direction (i.e., the first direction or the second direction). It is noted that numerous modifications and alterations of the actions of the actuating device 12 may be made while retaining the teachings of the disclosure.

In some other embodiments, the actuating device 12 can be a microelectromechanical system (MEMS) gas pump, and the surface of the material is micro-machined by means of dry and wet etching, so as to make an integrally formed miniature gas pump, which includes an inlet plate 121, a resonance membrane 122, an actuating membrane 123 and a piezoelectric membrane 124. The inlet plate 121 includes at least one inlet 1210 and a convergence chamber 1211. The resonance membrane 122 includes a flexible suspension structure made by a surface micromachining process. The resonance membrane 122 further includes a central aperture 1220. The actuating membrane 123 includes a hollow and suspension structure made by the surface micromachining process. The material of the actuating membrane 123 can be a metallic membrane or a polysilicon membrane. The actuating membrane 123 further includes a suspension part 1230, an outer frame 1231 and a plurality of the connection parts 1232, wherein a plurality of the vacant space 1235 are formed among the connection part 1232, the suspension part 1230 and the outer frame 1231. The piezoelectric membrane 124 can be a metal oxide membrane made by a sol-gel process. In the embodiment, the piezoelectric membrane 124 is attached on one surface of the suspension part 1230. The inlet plate 121, the resonance membrane 122 and the actuating membrane 123 are stacked on each other sequentially, and a compressing chamber 1221 is formed between the resonance membrane 122 and the actuating membrane 123, but not limited thereto. When the piezoelectric membrane 124 is enabled to drive the actuating membrane 123, the gas is inhaled into the convergence chamber 1211 through the plural inlets 1210 of the inlet plate 121 and transferred to the compressing chamber 1221 through the central aperture 1220 of the resonance membrane 122 and flows out from the vacant space 1235 of the actuating membrane 123. As a result, the ambient gas is introduced into the gas flow channel 18.

From the above descriptions, the present disclosure provides the actuating and sensing module. A pressure gradient is generated in the gas flow channel by enabling the actuating device, so as to inhale gas into the gas flow channel by passing through the first protective film and the gas inlet. After the gas is transferred through the first protective film, the moisture and dust contained in the gas are removed by the protective film. After the gas is filtered, the gas is fed into the actuating and sensing module through the gas inlet. The sensor adjacent to the gas inlet senses the gas in the gas flow channel at the first moment to obtain a sensed data of the gas surrounding the actuating and sensing module. The gas is further discharged out of the gas flow channel through the gas outlet. Under this circumstance, the gas is circulated along the gas flow path and the gas can be quickly transferred while achieving silent efficacy. Moreover, since the sensor is separate from the actuating device and is adjacent to the gas inlet, when the gas flows into the actuating and sensing module, it could be sensed at the first moment before it flows into the actuating device, so as to prevent the influence of the heat generating from the enabling process of the actuating device. Consequently, the detection accuracy of the sensor is enhanced by the apart arrangement between the actuating device and the sensor to prevent the interference of the actuating device to the sensor. In addition, due to the arrangement of the first protective film and the second protective film, it prevents the inner components from the damage and the rusty caused by the moisture or the accumulated dust. Consequently, the gas transportation efficiency is enhanced and the performance of the device with the actuating and sensing module is enhanced. Therefore, the actuating and sensing module of the present disclosure is industrially valuable.

While the disclosure has been described in terms of what is presently considered to be the most practical and preferred embodiments, it is to be understood that the disclosure needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module, comprising:
   a first substrate with at least one control circuit disposed thereon;
   a second substrate having a gas inlet and a gas outlet, wherein the second substrate and the first substrate are stacked on each other as a gas flow channel is formed therebetween, wherein the gas inlet, the gas flow channel and the gas outlet are in communication with each other to form a gas flow path;
   at least one actuating device disposed in the gas outlet of the second substrate and electrically connected to the at least one control circuit; and
   at least one sensor disposed in the gas flow path and misaligned with the gas inlet, wherein the sensor is spaced apart from the actuating device and is electrically connected to the at least one control circuit;
   wherein the actuating device and the sensor are electrically connected to the at least one control circuit so as to obtain a driving power and to calculate and process a sensed data generated by the sensor, and the actuating device is enabled to drive gas to flow from the exterior of the actuating and sensing module into the gas flow channel through the gas inlet, and the gas flows through the sensor and is discharged out through the gas outlet, so that the gas circulated in the gas flow path is monitored by the sensor.

2. The actuating and sensing module according to claim 1, wherein the first substrate comprises at least one control circuit formed on the first substrate by a semiconductor process.

3. The actuating and sensing module according to claim 1, wherein the sensor is disposed on the first substrate by a semiconductor process.

4. The actuating and sensing module according to claim 1, wherein the first substrate comprises a recess formed by a semiconductor process, and the first substrate and the second substrate are stacked on each other as the gas flow channel is formed between the recess of the first substrate and the second substrate.

5. The actuating and sensing module according to claim 1, wherein the sensor includes at least one selected from the group consisting of an oxygen sensor, a carbon monoxide sensor, a carbon dioxide sensor, a temperature sensor, an ozone sensor, a volatile organic compound sensor and a combination thereof.

6. The actuating and sensing module according to claim 1, wherein the actuating device is a microelectromechanical system gas pump and the microelectromechanical system gas pump comprises:
   an inlet plate including at least one inlet and a convergence chamber;
   a resonance membrane having a suspension structure and a central aperture, wherein the suspension structure is flexible and is made by a surface micromachining process;
   an actuating membrane having a hollow and suspension structure made by the surface micromachining process and comprising a suspension part, an outer frame and at least one connection part, wherein at least one vacant space is formed among the at least one connection part, the suspension part and the outer frame; and
   a piezoelectric membrane attached on a surface of the suspension part,
   wherein the inlet plate, the resonance membrane and the actuating membrane are stacked sequentially and a compressing chamber is formed between the resonance membrane and the actuating membrane, wherein while the piezoelectric membrane is enabled to drive the actuating membrane, the gas is inhaled through the at least one inlet, transferred and converged to the convergence chamber, transferred to the compressing chamber through the central aperture of the resonance membrane and discharged out through the at least one vacant space, by which the gas outside the actuating device is introduced in the gas flow channel.

7. The actuating and sensing module according to claim 6, wherein the actuating membrane includes one of a metallic membrane and a polysilicon membrane.

8. The actuating and sensing module according to claim 6, wherein the piezoelectric membrane includes a metal oxide membrane made by a sol-gel process.

9. The actuating and sensing module according to claim 6, wherein the microelectromechanical system gas pump is an integrally formed structure.

10. The actuating and sensing module according to claim 6, wherein the actuating and sensing module further comprises at least one first protective film and at least one second protective film, wherein the first protective film is disposed to cover one of the inlet and the gas inlet, and the second protective film is disposed to cover the gas outlet, wherein the first protective film and the second protective film include a waterproof, dustproof and gas-allowed film structure, respectively.

11. The actuating and sensing module according to claim 1, wherein the actuating device is a resonant-type piezoelectrically-actuated gas pump and the resonant-type piezoelectrically-actuated gas pump comprises:
   an inlet plate comprising at least one inlet and a convergence chamber;
   a resonance membrane including a suspension structure and comprising a central aperture;

an actuating membrane including a hollow and suspension structure and comprising a suspension part, an outer frame and at least one connection part, wherein at least one vacant space is defined among the at least one connection part, the suspension part and the outer frame; and a piezoelectric membrane attached on a surface of the suspension part, wherein the inlet plate, the resonance membrane and the actuating membrane are stacked sequentially and a compressing chamber is formed between the resonance membrane and the actuating membrane, wherein while the piezoelectric membrane is enabled to drive the actuating membrane, the gas is inhaled through the at least one inlet, transferred and converged to the convergence chamber, transferred to the compressing chamber through the central aperture of the resonance membrane and discharged out through the at least one vacant space, by which the gas outside the actuating device is introduced in the gas flow channel.

12. The actuating and sensing module according to claim 11, wherein the actuating and sensing module further comprises at least one first protective film and at least one second protective film, wherein the first protective film is disposed to cover one of the inlet and the gas inlet, and the second protective film is disposed to cover the gas outlet, wherein the first protective film and the second protective film include a waterproof, dustproof and gas-allowed film structure, respectively.

13. The actuating and sensing module according to claim 12, wherein the first protective film and the second protective film comply with Rating IP64 of International Protection Marking (IEC 60529).

14. The actuating and sensing module according to claim 12, wherein the first protective film and the second protective film comply with Rating IP65 of International Protection Marking (IEC 60529).

15. The actuating and sensing module according to claim 12, wherein the first protective film and the second protective film comply with Rating IP66 of International Protection Marking (IEC 60529).

16. The actuating and sensing module according to claim 12, wherein the first protective film and the second protective film comply with Rating IP67 of International Protection Marking (IEC 60529).

17. The actuating and sensing module according to claim 12, wherein the first protective film and the second protective film comply with Rating IP68 of International Protection Marking (IEC 60529).

18. An actuating and sensing module, comprising:

at least one first substrate with at least one control circuit disposed thereon;

at least one second substrate having at least one gas inlet and at least one gas outlet, wherein the second substrate and the first substrate are stacked on each other as at least one gas flow channel is formed therebetween, wherein the gas inlet, the gas flow channel and the gas outlet are in communication with each other to form at least one gas flow path;

at least one actuating device disposed in the gas outlet of the second substrate and electrically connected to the at least one control circuit; and at least one sensor disposed in the gas flow path and misaligned with the gas inlet, wherein the sensor is spaced apart from the at least one actuating device and is electrically connected to the at least one control circuit;

wherein the at least one actuating device and the at least one sensor are electrically connected to the at least one control circuit so as to obtain a driving power and to calculate and process a sensed data generated by the at least one sensor the actuating device is enabled to drive at least one gas to flow from the exterior of the actuating and sensing module into the gas flow channel through the gas inlet, and the gas flows through the sensor and is discharged out through the gas outlet, so that the gas circulated in the gas flow path is monitored by the sensor.

* * * * *